United States Patent [19]

Tsukamoto et al.

[11] Patent Number: 5,061,620
[45] Date of Patent: Oct. 29, 1991

[54] HUMAN HEMATOPOIETIC STEM CELL

[75] Inventors: Ann Tsukamoto, Palo Alto; Charles M. Baum, Menlo Park, both of Calif.; Yukoh Aihara, Hiratsuka, Japan; Irving Weissman, Palo Alto, Calif.

[73] Assignee: SyStemix, Inc., Palo Alto, Calif.

[21] Appl. No.: 502,616

[22] Filed: Mar. 30, 1990

[51] Int. Cl.[5] .......................... C12N 5/00; C12Q 1/00; G01N 33/53
[52] U.S. Cl. ................ 435/7.21; 435/240.2; 435/240.21
[58] Field of Search .............. 435/240.2, 240.21, 29, 435/240.25, 7.21

[56] References Cited

U.S. PATENT DOCUMENTS 4,714,680 12/1987 Civin ........................ 435/240.25

OTHER PUBLICATIONS

Müller-Sieberg et al. (1988), J. Exp. Med., vol. 167: 1825-1840.
Kurtzberg et al. (1989), PNAS: vol. 86: 7575-7579.
Folks et al. (1988), Science: vol. 242: 919-922.
Lu et al. (1987), Journal of Immunology: vol. 139: 1823-1829.
Lewinsohn et al., Blood: vol. 75: 589-595 (1990). .
Gishen et al. (1987), J. of Immunology 138: 2433-2438.

Primary Examiner—Elizabeth C. Weimar
Assistant Examiner—Gian Wang
Attorney, Agent, or Firm—Bertram I. Rowland

[57] ABSTRACT

Human hematopoietic stem cells are provided by separation of the stem cells from dedicated cells. The stem cells may than be maintained by regeneration in an appropriate growth medium. Means are provided for assaying for the stem cells as to their capability for producing members of each of the hematopoietic lineages.

7 Claims, No Drawings

HUMAN HEMATOPOIETIC STEM CELL

INTRODUCTION

1. Technical Field

The field of this invention is the isolation, regeneration and use of hematopoietic stem cells.

2. Background

Mammalian blood cells provide for an extraordinarily diverse range of activities. The blood cells are divided into several lineages, including lymphoid, myeloid and erythroid. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Despite the diversity of the nature, morphology, characteristics and function of the blood cells, it is presently believed that there is a single progenitor, which is capable of self regeneration and by exposure to growth factors becomes dedicated to a specific lineage.

The stem cell population constitutes only a small percentage of the total number of leukocytes in bone marrow. In particular, B cells (CD19+) and myeloid cells (CD33+) make up 80-90 % of the CD34+ population. In addition, at the present time it is not known how many of the markers associated with differentiated cells are also present on the stem cell. One marker which has been indicated as present on stem cells, CD34, is also found on a significant number of lineage committed progenitors. Another marker which provides for some enrichment of progenitor activity is Class II HLA (particularly a conserved DR epitope recognized by a monoclonal antibody designated J1-43). However, these markers are found on numerous lineage committed hematopoietic cells. In particular, B cells (CD19+) and myeloid cells (CD33+) make up 80-90% of the CD34+ population. Moreover, a combination of CD3, .8, 10, 15, 19, 20, and 33 will mark >90% of all CD34+ cells. Therefore, in view of the small proportion of the total number of cells in the bone marrow which are stem cells, the uncertainty of the markers associated with the stem cell as distinct from more differentiated cells, and the general inability to biologically assay for human stem cells, the identification and purification of stem cells has been elusive. Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Indeed, one injected cell should be able to reconstitute all of the hematopoietic lineages.

The Thy-1 molecule is a highly conserved protein present in the brain and hematopoietic system of rat, mouse and man. These species differentially express this antigen and the true function of this molecule is unknown. However, the Thy-1 molecule has been identified on rat and mouse hematopoietic stem cells. This protein is also present on human bone marrow cells and is useful for the selection of hematopoietic stem cells.

There is a strong interest in identifying the human hematopoietic stem cell. Having possession of the stem cell will allow for identification of growth factors associated with its self regeneration. In addition, there may be as yet undiscovered growth factors associated (1) with the early steps of dedication of the stem cell to a particular lineage; (2) the prevention of such dedication; and (3) the negative control of stem cell proliferation. The availability of stem cells would be extremely useful in bone marrow transplantation, as well as transplantation of other organs in association with the transplantation of bone marrow. Stem cells are important targets for gene therapy, where the inserted genes promote the health of the individual into whom the stem cells are transplanted. In addition, the ability to isolate the stem cell may serve in the treatment of lymphomas and leukemias, as well as other neoplastic conditions, e.g., breast cancer. Thus, there have been world-wide efforts toward isolating the human hematopoietic stem cell in substantially pure or pure form.

RELEVANT LITERATURE

U.S. Pat. No. 4,714,680 describes a composition comprising human stem cells. EPA 89.304651.6 describes the isolation of mouse stem cells. See also the references cited therein. Analysis for hematopoietic progenitors have been reported by Whitlock and Witte, *PNAS USA* (1982) 79:3608; and Whitlock et al., Cell (1987) 48:1009. Thy-1 is a surface marker of reconstituting rodent bone marrow stem cells (Berman and Bashe *Exp. Hematol.* (1985) 13:1952 and Goldschneider et al., *J. Exp. Med.* (1978) 148:1351). Muller-Sieburg et al., *Cell* (1986) 44:653 describe Thy-$^{lo}$Lin− mouse hematopoietic stem cells and the use of limit dilution.

SUMMARY OF THE INVENTION

Methods resulting in the isolation of substantially homogenous compositions of human hematopoietic stem cells are provided. The methods employ a predetermined separation regimen and bioassays for establishing the generation of each of the hematopoietic lineages from the isolated cells. The human stem cells find use: (1) in regenerating the hematopoietic system of a host deficient in stem cells, (2) in a host that is diseased and can be treated by removal of bone marrow, isolation of stem cells and treatment of individuals with drugs or irradiation prior to re-engraftment of stem cells, (3) producing various hematopoietic cells, (4) detecting and evaluating growth factors relevant to stem cell self-regeneration; and, (5) the development of hematopoietic cell lineages and assaying for factors associated with hematopoietic development.

DESCRIPTION OF THE SPECIFIC EMBODIMENTS

At least, substantially homogeneous human stem cell compositions are provided which may serve as the progenitors for all human hematopoietic cell lineages. The stem cells are identified by specific markers which are identified with monoclonal antibodies. The substantially homogenous composition may be obtained by selective isolation of cells free of markers associated with differentiated cells, while displaying epitopic characteristics associated with the stem cells, and by regeneration of the isolated stem cells in defined culture systems leading to different hematopoietic cell lineages.

The stem cells are characterized by both the presence of markers associated with specific epitopic sites identified by antibodies and the absence of certain markers as identified by the lack of binding of certain antibodies It is not necessary that selection is achieved with a marker specific for stem cells. By using a combination of negative selection (removal of cells) and positive selection (isolation of cells), a substantially homogeneous stem cell composition can be achieved.

If desired, a large proportion of differentiated cells may be removed by initially using a "relatively crude" separation. The source of the cells may be the bone marrow, fetal, neonate or adult or other hematopoietic cell source, e.g., fetal liver. For example, magnetic bead separations may be used initially to remove large numbers of lineage committed cells, namely major cell populations of the hematopoietic systems, including such lineages as T cells, B cells, (both pre-B and B cells), myelomonocytic cells, or minor cell populations, such as megakaryocytes, mast cells, eosinophils and basophils. Desirably, at least about 70%, usually at least 80% of the total hematopoietic cells will be removed. It is not essential to remove every dedicated cell class, particularly the minor population members at the initial stage. Usually, the platelets and erythrocytes will be removed prior to sorting. Since there will be positive selection in the protocol, the dedicated cells lacking the positively selected marker will be left behind. However, it is preferable that there be negative selection for all of the dedicated cell lineages, so that in the final positive selection, the number of dedicated cells present is minimized.

The stem cells are characterized by being for the most part $CD34^+$, $CD3^-$, $CD7^-$, $CD8^-$, $CD10^-$, $CD14^-$, $CD15^-$, $CD19^-$, $CD20^-$, $CD33^-$, Class II $HLA^+$ and $Thy\text{-}1^+$. A highly stem cell concentrated cell composition is $CD34^+$, $CD10^-$, $CD19^-$ and $CD33^-$, more particularly in addition $CD3^-$ and $CD8^-$, preferably in addition Class II $HLA^+$ and $Thy\text{-}1^+$. The $CD3^-$, $-8^-$, $10^-$, $19^-$, $20^-$ and $33^-$ will be referred to as $Lin^-$. The CD10/19 markers are associated with B cells, while the CD33 cell marker is associated with myeloid cells. The Thy-1 marker is absent on human T cells. Also, for human $CD34^+$ or Class II $HLA^+$, rhodamine 123 can divide the cells into high and low subsets. See Spangrude, (1989) Immunology Today 344-350 for a description of the use of rhodamine 123 with mouse stem cells. Preferably the cells are rhodamine low.

In order to obtain the subject stem cells, it is necessary to isolate the rare pluripotent human stem cell from the other cells in bone marrow or other hematopoietic source. Initially, bone marrow cells may be obtained from a source of bone marrow, e.g., tibiae, femora, spine, or other bone cavities. Other sources of human hematopoietic stem cells include embryonic yolk sac, fetal liver, fetal and adult spleen, and blood.

For isolation of bone marrow from fetal bone or other bone source, an appropriate solution may be used to flush the bone, which solution will be a balanced salt solution, conveniently supplemented with fetal calf serum or other naturally occurring factors, in conjunction with an acceptable buffer at low concentration, generally from about 5-25 mM. Convenient buffers include Hepes, phosphate buffers, lactate buffers, etc. Otherwise bone marrow may be aspirated from the bone in accordance with conventional ways.

Various techniques may be employed to separate the cells by initially removing cells of dedicated lineage. Monoclonal antibodies are particularly useful for identifying markers (surface membrane proteins) associated with particular cell lineages and/or stages of differentiation. The antibodies may be attached to a solid support to allow for crude separation. The separation techniques employed should maximize the retention of viability of the fraction to be collected. For "relatively crude" separations, that is, separations where up to 10%, usually not more than about 5%, preferably not more than about 1%, of the total cells present having the marker, may remain with the cell population to be retained, various techniques of different efficacy may be employed. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation include fluorescence activated cell sorters, which can have varying degrees of sophistication, e.g., a plurality of color channels, low angle and obtuse light scattering detecting channels, impedance channels, etc.

One procedure which may be used is in a first stage after incubating the cells from the bone marrow for a short period of time at reduced temperatures, generally about 4° C., with saturating levels of antibodies specific for a particular cell type, e.g., CD3 and 8 for T cell determinants, the cells may then be washed with a fetal calf serum (FCS) cushion. The cells may then be suspended in a buffer medium as described above and separated by means of the antibodies for the particular determinants, using various proteins specific for the antibodies or antibody-antigen complex.

Conveniently, the antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

Conveniently, after substantial enrichment of the cells lacking the mature cell markers, generally by at least about 50%, preferably at least about 70%, the cells may now be separated by a fluorescence activated cell sorter (FACS) or other methodology having high specificity. Multi-color analyses may be employed, with the FACS which is particularly convenient. The cells may be separated on the basis of the level of staining for the particular antigens. In a first separation, starting with at least about $1 \times 10^{10}$, preferably at least about $5 \times 10^{10}$ cells, the antibody for CD34 may be labeled with one fluorochrome, while the antibodies for the various dedicated lineages may be conjugated to a different fluorochrome. Fluorochromes which may find use in a multicolor analysis include phycobiliproteins, e.g., phycoerythrin and allophycocyanins, fluorescein, Texas red. While each of the lineages may be separated in a separate step, desirably the lineages are separated at the same time as one is positively selecting for CD34 and/or Class II HLA. Generally, the number of cells obtained will be fewer than about 1% of the original cells, generally fewer than about 0.5% and may be as low as 0.2% or less.

The cells may then be further separated by positively selecting for Thy+, where the cells will generally be fewer than 0.5% of the original cells, generally in the range of 0.01–0.5%. The cells may be selected against dead cells, by employing dyes associated with dead cells (propidium iodide, LDS). Desirably, the cells are collected in a medium comprising 2% fetal calf serum. Other techniques for positive selection may be employed, which permit accurate separation, such as affinity columns, and the like. The method should permit the removal to a residual amount of less than about 20%, preferably less than about 5%, of the non-stem cell populations.

The CD34+Lin− and the CD34+Lin−Thy-1+ have low side scatter and low forward scatter profiles by FACS analysis. Cytospin preparations show the stem cell to have a size between mature lymphoid cells and mature granulocytes. Cells may be selected based on light-scatter properties as well as their expression of various cell surface antigens.

While it is believed that the particular order of separation is not critical to this invention, the order indicated is preferred. Preferably, cells are initially separated by a coarse separation, followed by a fine separation, with positive selection of a marker associated with stem cells and negative selection for markers associated with lineage committed cells. This separation is followed by selection for a cellular composition having multi-lineage potential and enhanced self-regeneration capability.

Compositions having greater than 90%, usually greater than about 95% of human stem cells may be achieved in this manner, where the desired stem cells are identified by being Class II HLA and/or CD34+, Lin− and Thy-1+ and being able to provide for cell regeneration and development of members of all of the various hematopoietic lineages. Ultimately, a single cell could be obtained from a stem cell composition and be used for long term reconstitution of an immunodeficient human.

The subject compositions are found to provide for production of myeloid cells and lymphoid cells in appropriate cultures, cultures providing hydrocortisone for production of myeloid cells (associated with Dexter-type cultures) and B lymphocytes in cultures lacking hydrocortisone, (associated with Whitlock-Witte type cultures). In each of the cultures, mouse or human stromal cells are provided, which may come from various strains, AC3 or AC6, stromal cells derived from mouse or human fetal bone marrow by selection for the ability to maintain human stem cells, and the like. The medium employed for the culturing of the cells is conveniently a defined enriched medium, such as IMDM (Iscove's Modified Dulbecco's Medium), a 50:50 mixture of IMDM and RPMI, and will generally be composed of salts, amino acids, vitamins, $5 \times 10^{-5}$M 2-ME, streptomycin/penicillin and 10% fetal calf serum, and may be changed from time to time, generally at least about once to twice per week. Particularly, by transferring cells from one culture with hydrocortisone, to the other culture without hydrocortisone, and demonstrating the production of members of the different lineages in the different cultures, the presence of the stem cell and its maintenance is supported. In this manner, one may identify the production of both myeloid cells and B cells.

To demonstrate differentiation to T cells, one may isolate fetal thymus and culture the thymus for from 4–7 days at about 25° C., so as to substantially deplete the lymphoid population of the fetal thymus. The cells to be tested are then microinjected into the thymus tissue, where the HLA of the population which is injected is mismatched with the HLA of the thymus cells. The thymus tissue may then be transplanted into a scid/scid mouse as described in EPA 0 322 240, particularly transplanting in the kidney capsule.

For red blood cells, one may use conventional techniques to identify BFU-E units, for example methylcellulose culture (Metcalf (1977) In: Recent Results in Cancer Research 61. Springer-Verlag, Berlin, pp 1–227) demonstrating that the cells are capable of developing the erythroid lineage.

In identifying myeloid and B cell capability, conveniently, the population to be tested is introduced first into a hydrocortisone containing culture and allowed to grow for six weeks in such culture. The medium employed will comprise a 50:50 mixture of RPMI 1640 and IMDM containing 10% FCS, 10% horse serum, streptomycin/penicillin, glutamine and $5 \times 10^{-7}$M hydrocortisone. During the six week period, it would be anticipated that in the absence of progenitor cells, all of the mature cells would die. If at the end of six weeks, myeloid cells are still observed, one may conclude that there is a progenitor cell which is providing for the continuous differentiation to myeloid cells. At this time, one may then change the medium, so that the medium now lacks hydrocortisone, to encourage the growth of B cells. By waiting 3–4 weeks and demonstrating the presence of B cells by FACS analysis, one may conclude that the progenitor cells which previously were capable of producing myeloid cells are also capable of producing B cells. Human hematopoietic cells grown in the presence of hydrocortisone can be maintained for at least four months. Similarly, human hematopoietic cells grown in the absence of hydrocortisone contain B lymphocytes (CD19+), as well as myelomonocytic cells for at least four months. From these cultures, one may sort for CD34+ Lin− or Class II HLA+Lin−, which should provide a composition substantially concentrated in the progenitor hematopoietic stem cell. The CD34+Lin− or Class II HLA+Lin− cells obtained from these cultures can give rise to B cells, T cells and myelomonocytic cells in the assays described above.

A pluripotent human stem cell may be defined as follows: (1) gives rise to progeny in all defined hematolymphoid lineages; and (2) limiting numbers of cells are capable of fully reconstituting a seriously immunocompromised human host in all blood cell types and their progenitors, including the pluripotent hematopoietic stem cell by cell renewal. In the subject compositions, fewer than a total of $10^6$ cells, usually fewer than $10^5$ cells, will be used to reconstitute an immunocompromised human host. The number of cells is required to insure that appropriate seeding at an appropriate site occurs, where the stem cell may self-renew. The number of cells required which become seeded at a proper site for self-renewal will usually be fewer than 50 cells, and as few as about a total of 20 cells or fewer, are able to fulfill the conditions indicated above. Thus, based on the standards set for the earliest progenitor pluripotent stem cell, the subject compositions are capable of fulfilling these requirements. Furthermore, the subject cells based on analysis of bone marrow cells appear to be in a range of from about 0.01-0.1% of bone marrow cells.

Once stem cells have been isolated, they may be propagated by growing in conditioned medium from stromal cells, such as stromal cells that can be obtained from bone marrow, fetal thymus or fetal liver, and are shown to provide for the secretion of growth factors associated with stem cell maintenance, coculturing with such stromal cells, or in medium comprising maintenance factors supporting the proliferation of stem cells, where the stromal cells may be allogeneic or xenogeneic. Before using in the coculture, the mixed stromal cell preparations may be freed of hematopoietic cells employing appropriate monoclonal antibodies for removal of the undesired cells, e.g, with antibody-toxin conjugates, antibody and complement, etc. Alternatively, cloned stromal cell lines may be used where the stomal lines may be allogeneic or xenogeneic.

The subject cell compositions may find use in a variety of ways. Since the cells are naive, they can be used to fully reconstitute an irradiated host and/or a host subject to chemotherapy; or as a source of cells for specific lineages, by providing for their maturation, proliferation and differentiation into one or more selected lineages by employing a variety of factors, such as erythropoietin, colony stimulating factors, e.g., GM-CSF, G-CSF, or M-CSF, interleukins, e.g., IL-1, $-2$, $-3$, $-4$, $-5$, $-6$, $-7$, $-8$, etc., or the like, or stromal cells associated with the stem cells becoming committed to a particular lineage, or with their proliferation, maturation and differentiation.

The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication of particular lineages, or the like.

The stem cells may be used for the treatment of genetic diseases. Genetic diseases associated with hematopoietic cells may be treated by genetic modification of autologous or allogeneic stem cells to correct the genetic defect. For example, diseases such as B-thalassemia, sickle cell anemia, adenosine deaminase deficiency, recombinase deficiency, recombinase regulatory gene deficiency, etc. may be corrected by introduction of a wild-type gene into the stem cells, either by homologous or random recombination. Other indications of gene therapy are introduction of drug resistance genes to enable normal stem cells to have an advantage and be subject to selective pressure, e.g. the multiple drug resistance gene (MDR). Diseases other than those associated with hematopoietic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Alternatively, one may wish to remove a particular variable region of a T-cell receptor from the T-cell repertoire. By employing homologous recombination, or antisense or ribozyme sequence which prevents expression, the expression of the particular T-cell receptor may be inhibited. For hematotropic pathogens, such as HIV, HTLV-I and II, etc. the stem cells could be genetically modified to introduce an antisense sequence or ribozyme which would prevent the proliferation of the pathogen in the stem cell or cells differentiated from the stem cells.

Methods for recombination in mammalian cells may be found in Molecular Cloning, A Laboratory Manual (1989) Sambrook, Fritsch and Maniatis, Cold Spring Harbor, NY.

The cells may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors or stromal cells associated with stem cell proliferation and differentiation.

The following examples are offered by way of illustration and not by way of limitation.

EXPERIMENTAL

Materials and Methods

Antibodies. The antibodies to the various markers were obtained as follows: CD3, 8, 10, 14, 15, 19, 20, 34 (Becton-Dickinson) CD33 (Coulter Immunology), Thy-1 (Dalchau and Fabre, J. Exp. Med. (1979) 149:576). CD33 (IgG) and CD34 (IgM) were also obtained from I. D. Bernstein (Andrews et al., Blood (1986) 68, 1030). The CD3, $-8$, $-10$, $-14$, $-15$, $-19$, $-20$, $-33$ were purchased as FITC conjugates. The antibodies from Bernstein were detected using the appropriate anti-Ig conjugated to fluorescein or phycoerythrin or Texas red (Caltag). The Thy-1 antibody was a fluorescein, phycoerythrin or biotin conjugate, where the biotin conjugate was detected with Texas Red-avidin (Caltag).

Fluorescence Activated Cell Sorter (FACS) Analysis and Sorting.

A Becton-Dickinson FACS modified as described (Parks and Herzenberg, Meth. Enzymol. (1984) 108:197) was employed. The dual laser instrument allows four fluorescent parameters and two light scatter parameters to be recorded for each analyzed cell. Residual erythrocytes and dead cells and debris were excluded from analysis by light scattering gating and PI (propidium iodide) staining or by scattering alone in 4color analyses. Compensation for spatial overlaps of fluorescein and phycoerythrin, and fluorescein and propidium iodide was adjusted electronically as described (Parks and Herzenberg, (1984) supra). Four color stains were performed using several combinations of the same reagents conjugated to different fluorochromes to assure that the results were consistent regardless of the various spatial overlaps of the fluorochromes. In addition, the results of 4-color analyses were calibrated by comparison with data from 2- and 3- color analyses.

For cell sorting, the stained samples were maintained at 4° C. throughout the sorting procedure. Sorted drops were collected in RPMI 1640 containing 10% fetal calf serum (Hazelton Biologics Inc., Lenexa, KS). Two color sorts employed phycoerythrin to label CD34 and fluorescein to label LIN cells, with propidium iodide (PI) to label dead cells, with both signals being detected and excluded in a single FACS channel. Three color sorts employed Texas red to label CD34, phycoerythrin to label Lin cells and fluorescein to label Thy-1 cells. Following isolation of a cell population by FACS, the sample was diluted 1:1 in HBSS, centrifuged for 10 minutes at a RCF of 200 and resuspended in 50 or 100 $\mu$l of HBSS for hemocytometer counting.

The culture assays were performed as follows:

Various murine stromal cell lines were employed, three of which are described in Whitlock et al., *Cell* (1987) 48:1009–1021. Confluent stromal cell layers were maintained for up to 3–4 weeks without passage by changing of the tissue culture medium every 5–7 days. To passage, the stromal cell layers were washed 3 times with serum-free medium, then overlayed with 2.5 ml (T-25 flask) of 0.5 mg/ml collagenase-dispase (Boehringer-Mannheim, Indianapolis, IN) in serum-free medium. The cultures were allowed to incubate 15–30 minutes at 37° C.; then the cells in the enzyme-containing medium were collected and RPMI-1640 medium with serum added. The stromal cells were suspended by pipetting with a Pasteur pipet, then cultured directly at 1–5th to 1–50th the original cell concentration. In general, confluent stromal layers subcultured at 1:10 reached confluency again after 5–7 days. Subclones were obtained by limiting dilution culture from 30 to 0.3 cells per well. Human stromal cell lines were treated similarly.

Cell suspensions of human fetal bone marrow were prepared from long bones of fetuses from 16–20 week gestation. The bones are split lengthwise and the medullary cavity is scraped with a scalpel blade. The bones are then placed in a 1 mg/ml solution of collagenase/-dispase in RPMI-1640. The bones are incubated for 30 minutes at 37° C., after which time the medullary cavity is flushed with media (RPMI-1640 with Pen/Strep 2-ME and 5% FCS) to remove hematopoietic cells. Alternatively, bone marrow may be flushed from the marrow cavity without collagenase/dispase treatment.

Cell suspensions are prepared from livers of 16–20 week gestation fetuses. The liver is minced and then pipetted to release cells. The cell suspension is then placed on a Ficoll gradient to remove hepatocytes, red blood cells and debris. The hematopoietic cells are then harvested.

Adult bone marrow is obtained from marrow aspirates, which are treated to remove red blood cells before use.

Bulk cultures are obtained by placing the human cells on the previously established confluent layer of mouse or human stromal cell lines. From $3 \times 10^4$ to $2 \times 10^5$ cells per ml are placed on the stromal cells in either T-25 flasks or 6 well plates, by addition of 3 ml to each well of a 6 well plate or 5 ml to T-25 flask. A 50:50 mixture of RPMI-1640 and IMDM containing 50 $\mu$/ml penicillin/50 $\mu$g/ml streptomycin, 1 mM sodium pyruvate, 2 mM glutamine, $5 \times 10^{-5}$ 2-mercaptoethanol and 10% fetal calf serum is employed. For Dexter-type conditions, IMDM containing 50 $\mu$/ml penicillin/50 $\mu$g/ml streptomycin, 1 mM sodium pyruvate, 2 mM glutamine, 10% fetal calf serum, 20% horse serum and $10^{-6}$ M hydrocortisone sodium succinate is employed. Bone marrow cells grown in the Dexter-type medium give rise only to myeloid differentiation. Cultures were established with whole cell populations or cells fractionated by their expression of cell surface antigens (CD34, HLA-DR, Thy-1).

Limiting dilution cultures were prepared using 96 well plates containing the mouse stromal cells as confluent layers. The human cells were titered into the plates at progressively lower concentrations with at least 24 wells plated at each cell concentration. The plates were then examined to determine the percentage of positive wells at each cell number. The data is then plotted graphically.

One can determine the frequency of cells in the starting population which grow under the above defined conditions. The frequency is determined by the cell number at which 37% of the wells show no growth. In one study, 1/1500 of the unsorted cells respond while 1/40 of the CD34+ fraction and 1/4000 of the CD34− fraction respond.

AC3 and AC6 Cocultures

Cocultures established with the mouse bone marrow stromal cell lines, AC3 or AC6, have served successfully as feeder layers for human cultures and have inhibited fibroblast overgrowth at low cell densities.

(1) Cell suspensions from more than one hundred human fetal bone marrow, fetal liver, or adult bone marrow samples have been cocultured for up to 20 weeks with continuous production of hematopoietic cells during this time indicating that early human progenitors or stem cells have been established in these cultures.

(2) Cultures show small to medium sized human bone marrow cells attached to the mouse stromal cells and proliferation occurs over the first one to three weeks of culture; thereafter they remain fairly stable.

(3) Cells form loose aggregates consisting of non-adherent and adherent cells overlying stromal cells which in turn overlie small to intermediate sized cells (pseudo-emperiopoiesis). Overall, the appearance of the cultures is similar to mouse long-term cultures.

(4) Cytospin and Fluorescence Activated Cell Sorter (FACS) analyses show maintenance of human hemato-lymphoid cells. In the absence of hydrocortisone (Whitlock-Witte like conditions), cultures are a mixture of myeloid, monocytoid, and lymphoid lineages by morphology. The majority of cells are myeloid and vary from myeloblasts to mature polymorphonuclear cells. From 15–40% of the cells are mononuclear and many of these cells have a lymphoid morphology.

(5) Approximately 20–40% of the cells stain with the CD15 antibody and 10–50% of the cells stain with the B lineage markers, CD10, CD19, or CD20, indicating a significant number of B cells. Cells selected from fetal bone marrow for CD19 expression survive for less than three weeks in culture. The presence of CD10+ and CD19+ cells after >4 weeks in culture indicates that early B cells are arising from committed progenitors. In addition, from 1 to 10% of the cells stain for cytoplasmic $\mu$ heavy chain which confirms the presence of Pre-B cells. Significant numbers of cells express CD20 although less than 1% express sIg, indicating that few of the early B cells mature under the indicated culture conditions. Furthermore, cultures initiated after depletion of B cells (CD10, CD19) by cell sorting show B cell development within one week of culture initiation.

(6) Cultures initiated in the presence of hydrocortisone (Dexter-like conditions) have no detectable T or B cells and have a large percentage of granulocytes and myeloid cells as evidenced by FACS analysis and cytospins. The presence of mitotic figures and the long term maintenance of these cultures indicates the presence of some active progenitor cell. When these hydrocortisone containing cultures are switched to media without hydrocortisone, 2 to 6% CD19 cells can be found within two weeks. This data would further substantiate the presence of an active progenitor cell in this coculture system.

The following tables indicate the results for the in vitro culture assays.

weeks and screened for the presence of myeloid cells and B cells.

TABLE 3

KINETICS OF B CELL GENERATION IN VITRO AFTER FACS DEPLETION OF B CELLS (CD10+, CD19+) FROM FETAL BONE MARROW

| Days in vitro | Cell subset (K336) | CD10 | CD15 | CD19 | k/l | CD33 | CD34 |
|---|---|---|---|---|---|---|---|
| d8 | WBM | 72% | 43% | 65% | 5%/4% | 25% | 4% |
|  | 34+10+19+ | 95 | 14 | 95 | 4/1 | 5 | 4 |
|  | 34+10−19− | 40 | 61 | 32 | 0.1/0.1 | 65 | 6 |
| d15 | WBM | 31 | 34 | 42 | 6/8 | 37 | 3 |
|  | 34+10+19+ | 90 | 6 | 88 | 11/20 | 12 | 1 |
|  | 34+10−19− | 16 | 38 | 18 | 1/2 | 38 | 2 |
| d22 | WBM | 28 | 37 | 21 | 1/3 | 70 | .2 |
|  | 34+10+19+ | 20 | ND* | 20 | 4/12 | ND* | ND* |
|  | 34+10−19− | 31 | 43 | 23 | 1/2 | 73 | 4 |
| d29 | WBM | 49 | 39 | 32 | 1/2 | 54 | 21 |
|  | 34+10+19+ | ND* | ND* | 15 | 3/9 | 77 | ND* |
|  | 34+10−19− | 73 | 21 | 66 | 1/2 | 31 | 13 |
| d56 | WBM | ND | 19 | 7 | 0/0 | 81 | 3 |
|  | 34+10+19+ | ND | 2 | 0 | 0/0 | 50 | 4 |
|  | 34+10−19− | ND | 15 | 23 | 1/1 | 69 | 2 |

Numbers indicate the percentage of cells stained by the indicated MAb as determined by FACS.
*Indicates insufficient cells for analysis Alternatively, fetal WBM is separated by FACS into CD34+, 33−, 10−, 19− and the cells are grown in the absence of hydrocortisone. By employing limit dilution about 10-100 cells are found to be able to be maintained in the coculture for greater than six weeks and be differentiated into mature myeloid and B cells.

TABLE 1

ANTIGEN STAINING PROFILE OF NON-ADHERENT HUMAN CELLS GROWN IN THE CO-CULTURE SYSTEM WITHOUT HYDROCORTISONE

| Sample # | Time in Culture (Weeks) | CD10 (B cell) | CD19 (B cell) | CD20 (B cell) | CD34 (progenitor cell) | CD16 (myeloid) | Methylcellulose (col/$10^5$) |
|---|---|---|---|---|---|---|---|
| S133 | 0 |  |  |  |  |  | 200 |
|  | 7 | 24 | 14 | ND | 38 | ND |  |
|  | 9 | ND | 7 | 12 | 31 | ND | 92 |
|  | 12 | 45 | 29 | 33 | 46 | 45 | 115 |
|  | 14 | 21 | 8 | 13 | 18 | 22 | 120 |
| S143 | 0 |  |  |  |  |  | 156 |
|  | 3 | 31 | 18 | 15 | 36 | 40 | 84 |
|  | 5 | 39 | 21 | 34 | 65 | 42 | 96 |
|  | 8 | 19 | 15 | 45 | 51 | ND | 44 |
|  | 10 | 24 | 26 | 19 | 41 | 31 | 140 |

TABLE 2

| Sample # | Time in culture (weeks) | BONE MARROW UNDER DEXTER CONDITIONS | | | | |
|---|---|---|---|---|---|---|
|  |  | Condition | CD15 (mono/gran) | CD19 (B Cell) | CD33 myeloid | CD34 (progenitor cell) |
| K146 | 5 | +HC | 93.5 | 0.23 | 40.9 | 20.6 |
| K146 | 9 | +HC | 91.5 | ND | 90.5 | 68.3 |
| K146 | 7/2* | +HC/−HC | 84.6 | 6.0 | ND | 58.4 |
| K146 | 10 | +HC | 95.0 | 0.3 | 26.0 | 23.0 |

*Switch cultures — initiated in hydrocortisone, switched to media without hydrocortisone.

FACS separation of Fetal Bone Marrow (FBM) was performed dividing fractions into CD34+, 10+, 19+ and CD34+ 10−, 19−. The fractions are then grown continuously in the absence of hydrocortisone for eight entiated into mature myeloid and B cells.

TABLE 4

ANALYSIS OF B-LYMPHOID AND MYELOID CELLS IN VITRO CULTURES

| Cells (K283) | Time (days) | % CD10 (Early B Cell) | % CD19 (Pan-B Cell) | % k/l (Mature B) | % CD15 (Myeloid) | % CD34 (Progenitor) | GM Colonies $10^5$ | BFU-e/$10^5$ |
|---|---|---|---|---|---|---|---|---|
| WBM | 0 | 35 | 33 | 7/3 | 45 | 8 | 59 | 89 |
| 34+10+33+ | 0 | 70 | 60 | 10/4 | 35 | 98 | 1199 | 755 |
| 34+10−33− | 0 | 1 | 3 | 1/0.5 | 1 | 95 | 72 | 102 |
| WBM | 21 | 25 | 14 | 2.2/1.9 | 20 | 0.13 | 39 | 39 |
| 34+10+33+ | 21 | 12 | 1.7 | 0.2/0.2 | 39 | 1.9 | 1976 | 1576 |
| 34+10−33− | 21 | 52 | 49 | 8.2/4.9 | 31 | 0.4 | 1841 | 1685 |

The results of the CD34, 33, 10 separation are shown in Table 4. The sorted cell populations as well as the unsorted cells were analyzed at the time of separation (t=0) as well as twenty-one days (t=21) later. Analysis of the FACS staining profile at t=0 shows that myeloid and B cells were effectively removed from the CD34+CD10−CD33− cells with less than 5% contaminating B and myeloid cells. In contrast, by day 21 about 50% of the CD34+CD10−CD33− cells were B cells. In addition, there was a ten-fold increase in cell numbers between t=0 and t=21. Therefore, there was an overall 100-fold increase in B cells over the 21 day period. Further, about one-third of the B cells express sIg with a 1.5/1 ratio of kappa and lambda light chains. The results indicate that the B cells are polyclonal and do not represent an Epstein-Barr viral transformation. In comparison, the CD34+CD10+CD33+ cells show a dramatic decrease in B cells and total cell numbers over the 21 day period. The results show that the CD34+ cells which express CCD10 and/or CD19 are not long lived progenitors.

Myeloid cell differentiation was analyzed by FACS and methylcellulose assay. FACS analysis shows a 10 fold increase in mature myeloid cells in the CD34+CD10−CD33− cell subset. Analysis of the methylcellulose data showed that 90-95% of the CFU-GM and BRU-e activity is contained in the CD34+CD10+CD33+ cell subset at time zero. However, at day 21, the CD34+CD10+CD33+ and the CD34+CD10−CD33− cell populations have nearly equivalent CFU-GM AND BFU-E cell levels. Therefore, the CD34+CD10−CD33− cells have the capacity to give rise to B cells (CD19+, cytoplasmic μ+, sIg+), myeloid cells (CD15+, − 33+, CFU-GM)and erythroid cells (BFU-e) over 21 days in culture. Similar results are obtained when cells are separated on the basis of CD34,CD10,CD19,CD33 or CD34,CD3,CD7,CD8,CD10,CD14,CD15,CD19,CD20,CD33.

When CD34+ cells are divided into Thy-1+ and Thy-1− fractions and assayed in the methylcellulose assay, these two fractions give similar readouts as seen in Table 5. When assayed by limiting dilution and in the cocultures, the CD34+, Thy-1+ fraction is enriched for progenitor activity as evidenced by 1) the percentage of B cells generated in the coculture and 2) the frequency of responding cells in the limit dilution assay. (Tables 5 and 6) In order to obtain 75% positive wells in the limit dilution assay, the Thy-1+ fraction required approximately 1/30-1/50 cells whereas the Thy-1− fraction requires 1/170-1/500 cells. This indicates that the Thy-1+ fraction is further concentrated for the progenitor cell. Moreover, when assayed in the in vivo T cell assay, the Thy-1+ fraction gives rise to donor derived T cells, whereas the Thy-1− fraction does not.

TABLE 5

FREQUENCY AALYSIS OF CD34+ THY1 POPULATIONS IN METHYCELLULOSE AND LIMIT DILUTION ASSAYS

| Sample | Methycellulose Freq. of GM col | Limit Dilution Frequency | | |
|---|---|---|---|---|
| | | 21 days | 28 days | 35 days |
| K275 WBM | 1/10,000 | NA | 1/3000 | NA |
| CD34+Thy+ | 1/284 | " | 1/35 | " |
| CD34+Thy− | 1/312 | " | 1/170 | " |
| K306 WBM | 1/1430 | NA | NA | NA |
| CD34+Thy+ | 1/100 | 1/120 | 1/50 | NA |
| CD34+Thy− | 1/340 | <1/1000 | 1/500 | <1/800 |

TABLE 6

ANALYSIS OF CD34/THY-1 SUBPOPULATIONS IN LONG TERM CULTURES

| Cell Pop. | Time in culture | % CD10 (early B cell) | % CD19 (B cell) | % CD15 (myeloid) | % CD33 (myeloid) | CD34 (progenitor cell) |
|---|---|---|---|---|---|---|
| K299 WBM | 8 | 0.1 | 0.1 | 5.4 | 60.8 | 1.0 |
| CD34+Thy1+ | 8 | 31.0 | 37.0 | 42.7 | 20.2 | 0.3 |
| CD34+Thy1− | 8 | 0.5 | 0.4 | 9.0 | 28.1 | 0.4 |
| K332 WBM | 7 | 0.3 | 0.4 | 1.9 | 80.4 | 13.0 |
| CD34+Thy1+ | 7 | 49.0 | 43.4 | 20.0 | 57.7 | 3.5 |
| CD34+Thy1− | 7 | 7.4 | 8.2 | 3.1 | 76.4 | 2.6 |

The thymus assay for T cell generation was performed as follows. Fetal thymus fragments are obtained of about 1 mm$^3$ in size. The fragments are cultured in a thymus organ culture system at 25 degrees C. for 3-7 days to stimulate the in vitro receptivity of the thymus for precursor cells. The cell composition comprising about $10^2$–$10^4$ cells in a FCS containing balanced salt solution is injected at a volume of 1 μl using a glass micropipet linked to an oil-filled micrometric screw-operated syringe. Twenty-four hours after injection, the in vitro colonized thymus fragments are implanted under the kidney capsule of SCID mice. See EPA 0 322 240. The injected cells are HLA mismatched with the thymus. At intervals, recipient animals are sacrificed and the grafts harvested. Cell suspensions are analyzed in a tow-color immuno-fluorescence assay for the presence of donor derived T lymphocytes (CD3, 8+).

TABLE 7

T cell repopulation of the human thymus followinq in vitro colonization by microinjection of leukocyte/precursor cells and regrafting into SCID mice

| Presursor Cell Phenotype | Microinjected Cell Number | Repopulation (+/Total) |
|---|---|---|
| (FBM) CD34+ | $10^4$ | 9/11 |
| (FBM) CD34+ | $10^2$ | 2/4 |
| (FBM) CD34+, 7− | $10^4$ | 6 weeks: 3/5 |
| | | 11 weeks: 2/3 |
| (FBM) CD34+, 7+ | $10^4$ | 6 weeks: 3/4 |
| | | 11 weeks: 0/3 |
| (FBM) CD34+, Thy | $10^4$ | 2/3 |
| (FBM) CD34+, Thy− | $10^4$ | 0/2 |
| (HDC) CD34+ | $2 \times 10^3$ | 2/5 |
| (FL) HLA-DR+, Lin*− | $10^4$ | 11/14 |

FBM: Fetal Bone Marrow
HDC: Human Dexter Culture
FL: Fetal Liver
Lin* CD3, −8, −10, −15, −19, −20

The above results that a small population of selected cells give rise to T cells, resulting in terminally differentiated CD4+ and CD8$^{30}$ T-cells. The Thy-1− population does not appear to provide a detectable level of differentiated T-cells.

It is evident from the above results, that the subject invention provides for cells which are substantially homogenous in human hematopoietic stem cells. Thus, by appropriate selection with particular factors and the development of bioassays which allow for self regeneration of stem cells and screening of the stem cells as to their surface markers, a substantially homogenous viable human hematopoietic stem cell composition may be produced for a variety of purposes. The stem cells may be used in bone marrow transplants, where the cells may be freed of neoplastic cells. Further, the use of pure stem cells will prevent graft-versus-host disease. In addition, the cells may be modified by appropriate recombination, either homologous or non-homologous, to correct genetic defects or provide genetic capabilities naturally lacking in the stem cells, either as to the individual or as to stem cells generally. In addition, because the composition is substantially free of other cells, the stem cell composition may be used to isolate and define factors associated with regeneration and differentiation.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A cellular composition comprising human hematopoietic stem cells with fewer than 5% of lineage committed cells, wherein said hematopoietic stem cells are characterized as Thy-1+, capable of self-regeneration in a coculture medium and differentiation to members of the lymphoid and myelomonocytic hematopoietic lineages.

2. A cellular composition having at least 80% of the cells characterized by being human, hematopoietic and being CD34+10−19−33−.

3. A cellular composition according to claim 2, wherein said cells are further characterized by being Thy-1+.

4. A method for obtaining a cellular composition comprising human hematopoietic stem cells, wherein fewer than about 100 cells is capable of self regeneration in a coculture medium and differentiation to members of the lymphoid and myelomonocytic hematopoietic lineages, said method comprising:

separating a mixture of human hematopoietic stem and differentiated cells into a substantially homogeneous fraction comprising cells characterized by being human, hematopoietic and being CD34+10−19−33−.

5. A method according to claim 4, wherein said cells are further characterized by being Thy-1+.

6. A method according to claim 4, wherein said separation comprises:

combining said mixture with monoclonal antibodies conjugated to fluorescent labels to CD34, 10, 19 and 33, wherein said antibodies to 34 have a different fluorescent label from the other antibodies; and separating a cell fraction characterized by being CD34+10−19−33− by means of said fluorescent labels.

7. A method according to claim 6, comprising the additional step of combining said CD34+10−19−33− cell fraction with a fluorescent labeled monoclonal antibody to Thy-1; and isolating a Thy-1+ fraction.

* * * * *